United States Patent [19]

Wilson

[11] Patent Number: 4,809,530
[45] Date of Patent: Mar. 7, 1989

[54] COOLING BED RUN IN TABLE

[75] Inventor: Alexander I. Wilson, Sheffield, England

[73] Assignee: Morgan Construction Company, Worcester, Mass.

[21] Appl. No.: 128,038

[22] Filed: Dec. 3, 1987

[51] Int. Cl.[4] .................... B21B 43/00; B65G 47/26
[52] U.S. Cl. .................................................... 72/201
[58] Field of Search ................ 72/200, 201, 202; 198/448, 474.1, 614, 774; 414/748

[56] References Cited

U.S. PATENT DOCUMENTS 4,505,374  3/1985  Beerens et al. ............... 198/448

FOREIGN PATENT DOCUMENTS

| 2026896 | 12/1971 | Fed. Rep. of Germany | 72/201 |
| 1303558 | 3/1972 | Fed. Rep. of Germany | 72/201 |
| 2425884 | 12/1975 | Fed. Rep. of Germany | 72/201 |
| 716661 | 2/1980 | U.S.S.R. | 72/201 |
| 747550 | 7/1980 | U.S.S.R. | 72/201 |

Primary Examiner—E. Michael Combs
Attorney, Agent, or Firm—Samuels, Gauthier, Stevens & Kehoe

[57] ABSTRACT

A rolling mill run-in table has at least two parallel paths extending alongside the receiving end of a cooling bed. First and second slide members extend respectively along each path on the side thereof closest to the cooling bed. First and second unitary lift assemblies extend respectively along the opposite side of each path. Each lift assembly has a side channel opening laterally towards the cooling bed. An underlying operating mechanism alternately adjusts the left assemblies between lowermost positions at which their side channels are closed by the adjacent slide members and aligned with the respective paths to confine product lengths moving axially therealong, and elevated positions at which the side channels are above the receiving paths and clear of the adjacent slide members to accommodate lateral discharge of the product lengths onto the receiving end of the cooling bed.

12 Claims, 3 Drawing Sheets

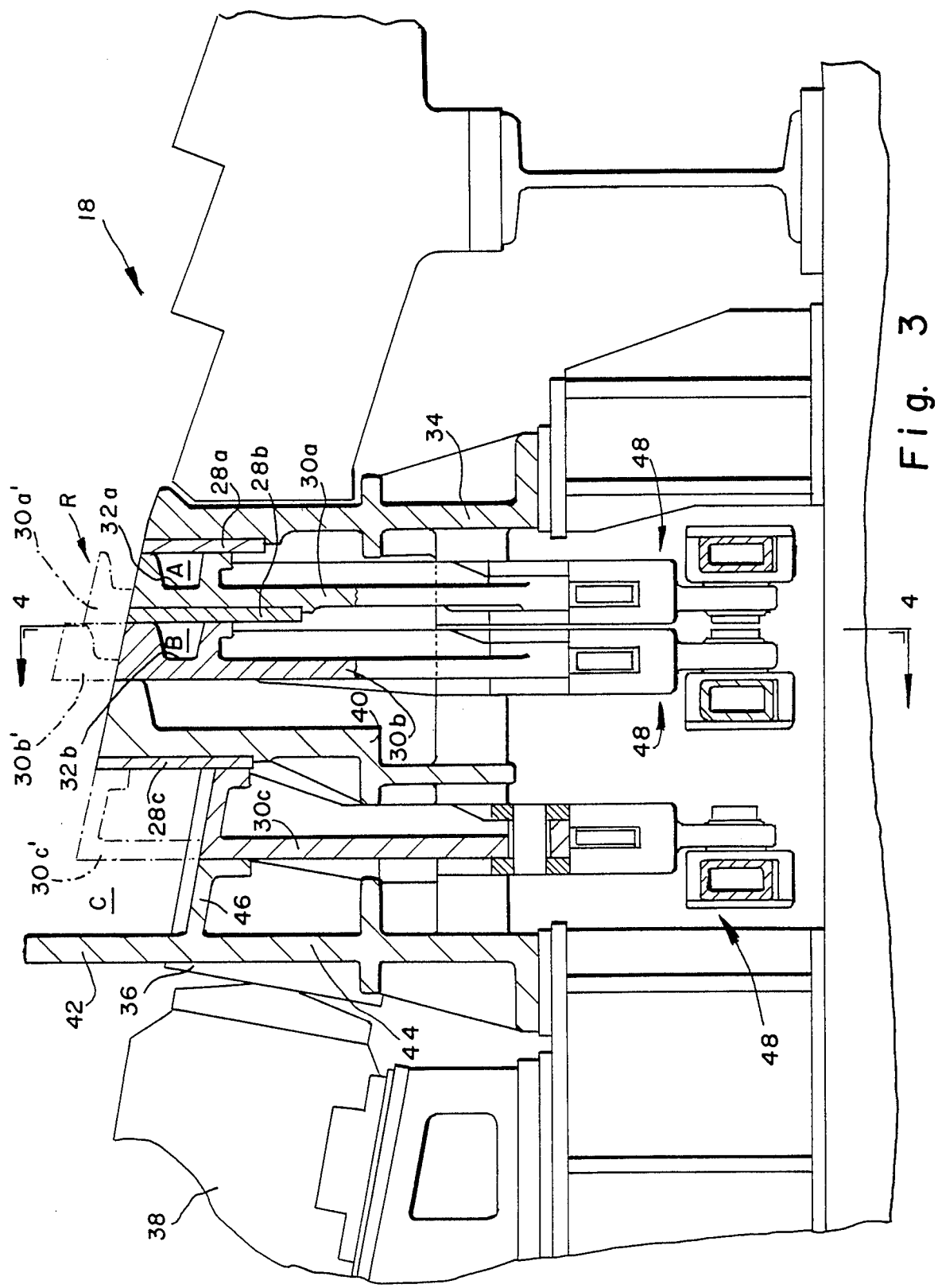

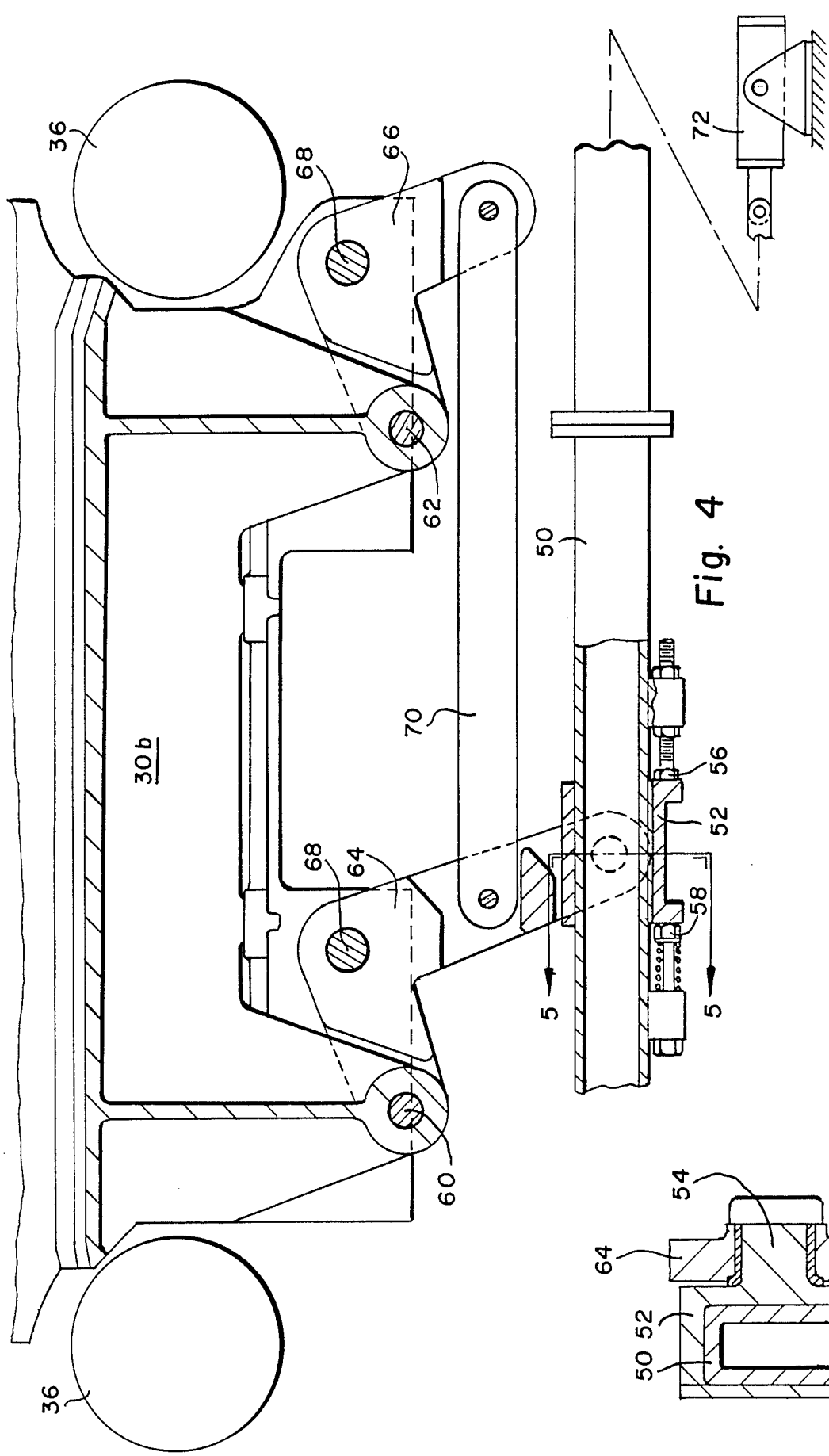

COOLING BED RUN IN TABLE

BACKGROUND OF THE INVENTION

This invention relates generally to material handling equipment for longitudinally receiving hot rolled products from a rolling mill, and for laterally transferring such products onto the receiving end of a carryover cooling bed.

The invention is particularly suited for although not limited to the handling of smaller sized products, such as for example round bars ranging in diameter from about 8 to 20 mm, as well as comparably sized shaped products such as angles, squares, etc. Such products normally exit from the mill at speeds on the order of 10 m/sec. and higher, and at elevated temperatures above about 900° C. Under these conditions, the products are quite limber and are very susceptible to bending, kinking and cobbling.

FIG. 1 is illustrative of a typical equipment layout at the delivery end of a rolling mill. The hot rolled products exit from the finishing mill 10 and are subdivided by a conventional switch/shear combination 12 into shorter lengths which are alternately directed along first and second parallel paths A, B. Decelerators 14a, 14b which typically may comprise conventional pinch rolls, decelerate the subdivided product lengths as they are received on a run-in table 16. After coming to rest, the product lengths are transferred from the run-in table onto a carryover cooling bed 18, where they are progressively shifted laterally in the direction of arrow 20 as they undergo cooling prior to further processing.

FIG. 2 is illustrative of a conventional prior art run-in table. Here, a hollow support beam 22 extends longitudinally over the receiving end of the carryover cooling bed 18. The cooling bed is of well known conventional design, having mutually spaced stationary racks 18' with cyclically movable carryover racks 18" interspersed therebetween. The beam 22 is suspended from an overlying support structure 24, and cooling water is circulated through its interior. Pivotal side flaps 26 cooperate with opposite sides of the beam to enclose the first and second parallel guide paths A, B along which successive longitudinally moving product lengths are alternately deflected by the upstream switch/shear combination 12. After the product lengths slide to a stop in their respective guide paths, the side flaps are opened (as indicated at the right hand side of FIG. 2) to thereby drop the product lengths through a distance of about 450–600 mm. onto the spaced racks of the underlying cooling bed.

A major problem with this type of arrangement is that when handling smaller products such as for example 8 or 10 mm. round bars, the vertical drop from the guide paths A, B onto the cooling bed racks is often enough to put a series of kinks into the bars. This design is also unduly complicated by its overhead support structure, which usually includes a cumbersome array of heavy stanchions and girders. In addition, the operating mechanisms employed to manipulate the side flaps 26 are prone to seizing up as a result of exposure to heat rising from hot bars being transferred across the underlying table.

SUMMARY OF THE INVENTION

A general objective of the present invention is to provide an improved run-in table incorporating novel features which avoid or at least substantially minimize the above-mentioned problems.

A more particular objective of the present invention is to avoid dropping and thus kinking or otherwise deforming the product lengths while transferring them onto the receiving end of the cooling bed.

A further objective of the present invention is to locate the operating mechanisms of the run-in table beneath the path of lateral product transfer, thereby eliminating cumbersome overhead support structures while at the same time safeguarding such operating mechanisms from seizing up as a result of overheating.

Still another objective of the present invention is to enable products to be cleared from respective adjacent channels of the run-in table while the products are still moving forwardly, thus making it possible to realize significant reductions in cycle time.

In a preferred embodiment of the invention to be described hereinafter in greater detail, these and other objectives and advantages are achieved by providing a run-in table with at least two parallel paths extending alongside the receiving end of the cooling bed. First and second elongated flat-surfaced slide members extend respectively along each path on the side thereof which is closest to the cooling bed. First and second lift assemblies extend respectively along the opposite side of each path. Each lift assembly has a side channel opening laterally towards the cooling bed. An underlying operating mechanism alternately adjusts the lift assemblies between lowermost positions at which their side channels are enclosed by the adjacent slide members and aligned with the respective paths to confine product lengths moving axially therealong, and elevated positions at which the side channels are above the receiving paths and clear of the adjacent slide members to thereby accommodate lateral discharge of the product lengths onto the receiving end of the cooling bed. In the course of being laterally discharged onto the cooling bed, the product lengths are continuously supported while moving down an inclined ramp defined by laterally adjacent components of the run-in table.

BRIEF DESCRIPTION OF THE DRAWINGS

FIG. 3 is a sectional view similar to FIG. 2 but showing a run-in table in accordance with the present invention;

FIG. 4 is a sectional view taken along line 4—4 of FIG. 3;

FIG. 5 is a sectional view taken along line 5—5 of FIG. 4.

DETAILED DESCRIPTION OF PREFERRED EMBODIMENT

Figure 1:
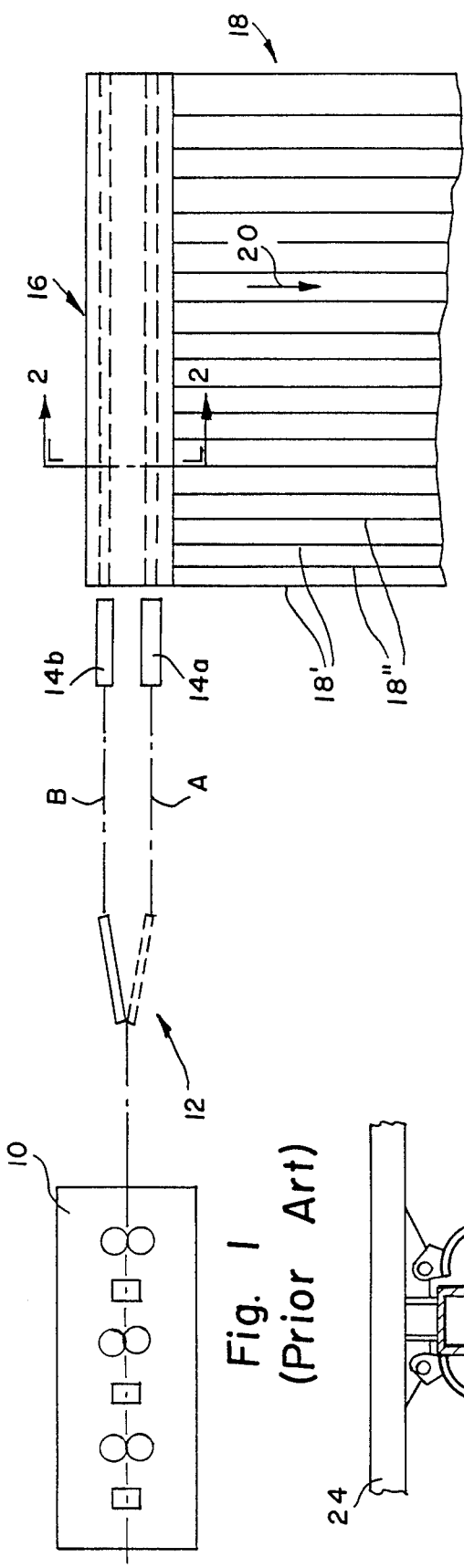
FIG. 1 is a schematic illustration of a typical equipment layout at the delivery end of a rolling mill.
Figure 2:
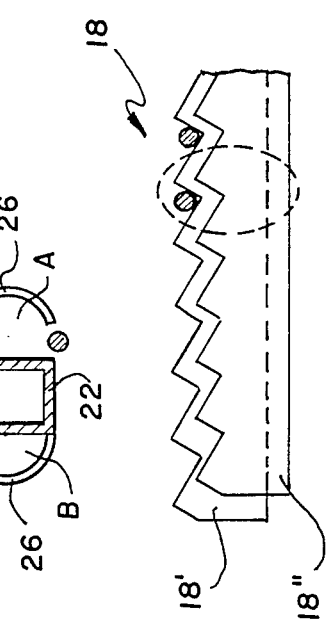
FIG. 2 is a sectional view on an enlarged scale taken along line 2—2 of FIG. 1 and showing a conventional prior art run-in table overlying the delivery end of the cooling bed.

Referring now to FIGS. 3–5, it will be seen that the run-in table of the present invention defines multiple parallel paths A, B and C running alongside the receiving end of a conventional carryover cooling bed 18. First, second and third elongated flat-surfaced slide members 28a, 28b and 28c extend respectively along the paths A, B and C on the sides thereof closest to the cooling bed. First and second lift assemblies 30a, 30b extend respectively along the opposite sides of the paths A, B. The first and second lift assemblies 30a, 30b are respectively provided with side chanels 32a, 32b opening towards the cooling bed.

The first slide members 28a are fixed and comprise integral parts of an inner side structure 34 of the run-in table adjacent to the cooling bed, whereas the second slide members 28b are carried on the first lift assemblies 30a. The side channels 32a, 32b are preferably provided with bottom surfaces which are inclined downwardly towards the cooling bed.

The first and second guide paths A, B are designed to handle the previously described smaller higher speed mill products. Larger slower moving mill products, e.g., bars larger than 20 mm in diameter, are directed along the third path C over inclined table rollers 36 driven by motors 38.

The sides of the third path C are defined by the third slide members 28c which comprise integral parts of an intermediate support structure 40 of the run-in table, and by side plates 42 on an outer side structure 44 of the table. The bottom of the third path between the table rollers 36 is defined by flanges 46 of the outer support structure 44, and by the top surfaces of third lift assemblies 30c.

The top surfaces of the first and second lift assemblies 30a, 30b as well as the top surfaces of the support structures 34, 40 and the top edges of the slide members 28a, 28b and 28c are inclined downwardly towards the cooling bed to provide a substantially continuous ramp R leading from the third path C to the first notch of the cooling bed 18.

The first, second and third lift assemblies 30a, 30b and 30c are vertically adjustable between their lowered positions as indicated by the solid lines in FIG. 3, and elevated positions indicated by the broken lines at 30a', 30b' and 30c'. Such vertical adjustments are carried out by underlying operating mechanisms generally indicated at 48.

As can best be seen in the FIGS. 4 and 5, the operating mechanism for each lift assembly 30a-30c includes a draw bar 50 extending along the length of and beneath the run-in table. The draw bar carries collars 52 having laterally projecting stub shafts 54. One collar is provided for each section of the lift assembly. The collars are capable of limited movement along the length of the draw bar between adjustable stops 56 and spring loaded stops 58.

Each lift assembly is pivotally connected as at 60 and 62 to a pair of bell cranks 64, 66. The bell cranks are in turn each pivotally connected as at 68 to an adjacent support structure of the run-in table. The depending leg of bell crank 64 is pivotally connected to the stub shaft 54 of the respective collar 52. A link 70 extends between and is pivotally connected to the depending legs of both bell cranks 64, 66.

A conventional reciprocating mechanism, which may for example include a linear actuator 72 or the like, is employed to axially reciprocate the draw bar 50. As viewed in FIG. 4, when the draw bar is shifted to the left, the lift assembly is elevated, whereas shifting of the draw bar to the right lowers the left assembly.

In light of the foregoing, it will now be appreciated by those skilled in the art that the run-in table of the present invention is particularly suited to the efficient handling of small products issuing from the mill at relatively high speeds. Such products are alternately directed along the first and second paths A, B where they are fully and safely confined within the side channels 32a, 32b which are closed by the respective associated slide members 28a, 28b. As soon as a product length in the first path A approaches a full stop, the first lift assembly 30a is elevated to the position indicated at 30a'. This allows the product while it is still moving forwardly, to roll or slide down the adjacent portion of the inclined ramp surface R into the first notch of the cooling bed. While this is happening, another product length can be coming to a stop along the second path B. When the first path A is clear, the first lift assembly 30a is lowered and at the appropriate time, the second lift assembly 30b is raised to the position 30b', thereby allowing the product in channel 32b to move laterally down the inclined ramp surface R towards the cooling bed. Each product length is fully supported by the ramp surface R during its lateral travel to the cooling bed. Thus, kinking is eliminated.

When larger products have been received along the third path C and have come to a stop, the third lift assemblies 30c are elevated to the positions indicated at 30c', thereby again allowing the product lengths to move laterally downwardly across the ramp surface R to the cooling bed.

The operating mechanisms for manipulating the lift assemblies, as well as the associated table support structures, are all located to one side of and beneath the operating level of the cooling bed. Thus, in comparison to prior art arrangements, the cooling bed is unobstructed by cumbersome overhead structures.

The operating mechanisms are located beneath the path of lateral product transfer and are thus far less likely to become overheated.

I claim:

1. In a rolling mill wherein successive hot rolled product lengths are alternately directed longitudinally along at least first and second parallel paths, a run-in table for receiving such products and for effecting a lateral transfer thereof onto a cooling bed, said run-in table comprising:

first and second slide members extending respectively along said first and second paths on the sides thereof which are closest to the cooling bed;

first and second unitary lift assemblies extending respectively along the opposite sides of said paths, said lift assemblies each having integrally associated guide surfaces defining side channels opening laterally towards the cooling bed; and operating means for alternately adjusting said first and second lift assemblies between lowermost positions at which said side channels are closed by the respective slide members and aligned with the respective paths to laterally confine product lengths axially moving therealong, and elevated positions at which said side channels are above the respective receiving paths and clear of the respective slide members to thereby accommodate a lateral discharge of product lengths from said open side channels towards the cooling bed.

2. The run-in table of claim 1 wherein said second slide members are carried on said first lift assemblies.

3. The run-in table of claim 1 wherein said side channels have bottom surfaces inclined downwardly towards the cooling bed.

4. The run-in table of claim 1 wherein at least said first lift assemblies have top surfaces which are inclined downwardly towards the cooling bed, and across which product lengths move when being discharged from the side channels of said second lift assemblies.

5. The run-in of claim 2 wherein said first and second lift assemblies and said first and second slide members have top surfaces which are inclined downwardly towards the cooling bed, said top surfaces being arranged to define at least part of a substantially continuous inclined ramp leading downwardly towards the cooling bed when both of said lift assemblies are adjusted to the lowermost positions.

6. The run-in table of claim 5 wherein successive product lengths are optionally directed along a third path, with said first and second paths being located between said third path and said cooling bed, said run-in table further comprising third lift assemblies means for laterally shifting product lengths from said third path onto said inclined ramp for continued lateral movement thereacross to the cooling bed.

7. The run-in table of claim 6 wherein lateral movement of product lengths across said inclined ramp may be temporarily interrupted by elevating either of said first or second lift assemblies.

8. The run-in table of claim 1 wherein said first and second lift assemblies are in slidable contact respectively with said first and second slide members.

9. The run-in table of claim 8 wherein said first slide member is vertically fixed, and wherein said second slide member comprises an integral part of and is vertically adjustable with said first lift assembly.

10. The run-in table of claim 1 wherein said first and second lift assemblies have top surfaces inclined downwardly towards the cooling bed, and wherein said side channels have bottom surfaces which also are inclined downwardly towards the cooling bed.

11. Apparatus for receiving successive longitudinally moving hot rolled product lengths from a rolling mill and for laterally transferring such product lengths to a cooling bed, said apparatus comprising:
 means for longitudinally directing said product lengths alternately to one or the other of two parallel receiving paths extending past said cooling bed;
 first and second slide members respectively extending along each receiving path on the side thereof which is closest to said cooling bed;
 first and second unitary lift assemblies respectively extending along the opposite side of each receiving path, said lift assemblies each having integrally associated guide surfaces defining side channels opening towards said cooling bed; and
 operating means for alternately adjusting said first and second lift assemblies between lowermost positions at which said side channels are closed by the respective slide members and aligned with the respective receiving paths to laterally confine product lengths moving axially therealong, and elevated positions at which said side channels are above the respective receiving paths and clear of the respective slide members to accommodate a lateral discharge of product lengths from said open side channels onto the cooling bed.

12. A run-in table for receiving successive longitudinally moving hot rolled product lengths from a rolling mill and for laterally transferring such product lengths to the receiving end of a cooling bed, said run-in table comprising:
 first and second laterally spaced vertically disposed slide surfaces extending longitudinally along said receiving end;
 first and second unitary lift assemblies respectively arranged adjacent to said first and second slide surfaces, said lift assemblies each having integrally associated guide surfaces defining side channels opening towards said receiving end; and
 operating means for alternately adjusting said first and second lift assemblies between lowermost receiving positions at which said side channels are closed by the respective adjacent slide surfaces to substantially completely surround product lengths longitudinally received therein; and elevated transfer positions at which said side channels are clear of the respective adjacent slide surfaces to thereby accommodate lateral discharge of said product lengths to said receiving end.

* * * * *